United States Patent [19]
Peik et al.

[11] Patent Number: 5,166,335
[45] Date of Patent: Nov. 24, 1992

[54] HETEROPOLYSACCHARIDE S-184

[75] Inventors: Jerry A. Peik, San Diego; Suzanna M. Steenbergen, Alpine; George T. Veeder, San Diego, all of Calif.

[73] Assignee: Merck & Co., Inc., Rahway, N.J.

[21] Appl. No.: 579,229

[22] Filed: Sep. 4, 1990

Related U.S. Application Data

[63] Continuation of Ser. No. 243,529, Sep. 12, 1988, abandoned, which is a continuation of Ser. No. 750,806, Jun. 28, 1985, abandoned.

[51] Int. Cl.$^5$ .................. C07G 17/00; C02P 19/04; C02N 1/20
[52] U.S. Cl. .................. 536/123; 536/55.1; 435/101; 435/839
[58] Field of Search ............... 536/123, 55.1; 435/101, 435/839

[56] References Cited

U.S. PATENT DOCUMENTS

| | | | |
|---|---|---|---|
| 4,269,939 | 5/1981 | Kang et al. | 435/101 |
| 4,357,423 | 11/1982 | Cox et al. | 435/101 |
| 4,401,760 | 8/1983 | Peik et al. | 435/101 |
| 4,454,316 | 6/1984 | Veeder et al. | 435/101 R |
| 4,529,797 | 7/1985 | Peik et al. | 435/101 |

FOREIGN PATENT DOCUMENTS

| | | | |
|---|---|---|---|
| 079038 | 5/1983 | European Pat. Off. | 435/101 |
| 25390 | 10/1972 | Japan . | |

OTHER PUBLICATIONS

Chem. Abstract, vol. 96, 4951r.
Chem. Abstract, vol. 78, 5645d.
Lacok, P. et al., Biologia (Bratislava), 37(3), pp. 301-304 (1982).
Ghai, S. et al., J. Gen. Microbiol., 122(1), pp. 33-40 (1981).

*Primary Examiner*—Irene Marx
*Attorney, Agent, or Firm*—Charles M. Caruso; Richard S. Parr; Gabriel Lopez

[57] ABSTRACT

A novel heteropolysaccharide S-184 is disclosed. The compound is a gum produced under suitable conditions by the novel microorganism *Alcaligenes sp.* This new heteropolysaccharide is composed primarily of carbohydrate as uronic acid (7% to 16%) and mannose, glucose, and galactose in the molar ratio of 1:3:5. The non-carbohydrate portion contains 12–16% protein and 3–4.5% acyl groups. The compound is used to alter viscosity and rheology of aqueous solutions.

2 Claims, No Drawings

HETEROPOLYSACCHARIDE S-184

This application is a continuation of U.S. Ser. No. 07/243,529 filed on Sep. 12, 1988 (abandoned) which is a continuation of U.S. Ser. No. 06/750,806 filed on Jun. 28, 1985 (abandoned).

BACKGROUND OF THE INVENTION

This invention pertains to the field of microbial polysaccharides. In this field, it is known that a common feature of certain microorganisms is the production of exocellular heteropolysaccharides. Heteropolysaccharides are high molecular weight generally linear carbohydrate polymers containing two or more kinds of monosaccharides that form a repeating unit that is polymerized.

The usefulness of most heteropolysaccharides is based on their ability to alter the viscosity and rheology of aqueous solutions. In addition, heteropolysaccharides have related secondary functions, such as emulsification, suspension, stabilization, flocculation, lubrication, film-formation, etc.

Heteropolysaccharides are Widely used in food, well drilling, agricultural and a wide variety of other industrial applications. Commercial demand for these water soluble gums has greatly increased over the last few decades. Furthermore, new industrial techniques create a need for heteropolysaccharides with new physical properties. Consequently, the need for heteropolysaccharides with different functionality ranges, coupled with commercial demand, has clearly indicated the necessity for the development of new heteropolysaccharides with new and different physical properties.

It is, therefore, an object of the present invention to provide a new heteropolysaccharide, which is produced by a new Alcaligenes species. It is an additional object of the present invention to provide a method for making this new heteropolysaccharide. It is another object to provide microorganisms for making the new compound. A still further object is the provision of formulations containing the new heteropolysaccharide. These and other objects of the invention will be apparent from the ensuing description.

SUMMARY OF THE INVENTION

It has now been found that a novel heteropolysaccharide, composed principally of carbohydrate, from 12% to 16% protein and from 3.0% to 4.5% (calculated as acetic acid) acyl groups, the carbohydrate portion containing from about 7% to 16% uronic acid and the neutral sugars mannose, glucose and galactose in the approximate molar ratios of 1:3:5, is produced by the action of a new Alcaligenes species on a selected carbon source. This novel compound is prepared by aerobic fermentation of a suitable aqueous nutrient medium with an unnamed Alcaligenes species. A deposit under the Budapest Treaty of a biologically pure culture of this organism was made with the American Type Culture Collection Rookville, Md., on Jun. 19, 1985, under Accession No. ATCC 53160. This heteropolysaccharide, referred to herein as heteropolysaccharide S-184, has desirable properties in aqueous systems and is especially useful in foods.

DETAILED DESCRIPTION OF THE INVENTION

The novel organism of the present invention was isolated from a water sample collected from Pauma Creek on Palomar Mountain in San Diego, Calif. The organism was picked as a gummy colony from a YM agar plate after 4 days of incubation at 30° C. The isolate was then pure cultured on nutrient agar.

A flask seed was started from a nutrient agar culture of the isolate. This seed was then used to inoculate another flask containing a nutrient medium having hydrolyzed starch as the carbon source. After incubation, this flask was noted to contain a viscous beer and upon addition of isopropyl alcohol a fibrous material was precipitated. Another flask seed was started and used to determine the effect of various nutrient media on gum production and to determine the best growth media and fermentation conditions for this microorganism.

Fermentation Conditions

Heteropolysaccharide S-184 is produced during the aerobic fermentation of suitable aqueous nutrient media under controlled conditions via inoculation with a culture of the organism ATCC 53160. The media contain sources of assimilable carbon, nitrogen, and inorganic salts.

In general, carbohydrates (for example, glucose, fructose, maltose, xylose, and the like) can be used either alone or in combination as sources of assimilable carbon in the nutrient medium. The exact quantity of the carbohydrate source or sources utilized in the medium depends in part upon the other ingredients of the medium but, in general the amount of carbohydrate usually varies between about 2% and 5% by weight of the medium. These carbon sources may be used individually or combined in the medium.

Generally, many proteinaceous materials may be used as nitrogen sources for the fermentation process. Suitable nitrogen sources include, for example, yeast hydrolysates, primary yeast, soybean meal, cottonseed flour, hydrolysates of casein, cornsteep liquor, distiller's solubles or tomato paste and the like. The sources of nitrogen, either alone or in combination, are used in amounts preferably ranging from about 0.05% to 0.2% by weight of the aqueous medium.

Among the nutrient inorganic salts which can be incorporated in the culture media are the customary salts capable of yielding sodium, potassium, ammonium, calcium, phosphate, sulfate, chloride, carbonate, and the like ions. Also included are trace metals such as cobalt, manganese, iron and magnesium.

It should be noted that the nutrient media described herein are merely illustrative of the wide variety of media which may be employed, and are not intended to be limiting.

As an alternate medium, S-184 may be grown under low calcium ion conditions, i.e., in deionized water or some other aqueous system substantially free of calcium ions (i.e., less than about 4 ppm $Ca^{++}$ per 1% gum in the final fermentor broth).

The fermentation is carried out at temperatures ranging from about 25° C. to 35° C.; however, for optimum results it is preferable to conduct the fermentation at temperatures of from about 28° C. to 32° C. The pH of the nutrient media for growing the ATCC 53160 culture and producing the heteropolysaccharide S-184 can Vary from about 6 to 8.

Although S-184 is produced by both surface and submerged culture, it is preferred to carry out the fermentation in the submerged state.

A small scale fermentation is conveniently carried out by inoculating a suitable nutrient medium with the culture and, after transfer to a production medium, permitting the fermentation to proceed at a constant temperature of about 30° C. on a shaker for several days.

The fermentation is initiated in a sterilized flask of medium via one or more stages of seed development. The nutrient medium for the seed stage may be any suitable combination of carbon and nitrogen sources, however, the preferred carbon source is glucose or hydrolyzed starch. The seed flask is shaken in a constant temperature chamber at about 30° C. for 1-2 days, or until growth is satisfactory, and some of the resulting growth is used to inoculate either a second stage seed or the production medium. Intermediate stage seed flasks, when used, are developed in essentially the same manner; that is, part of the contents of the flask from the last seed stage are used to inoculate the production medium. The inoculated flasks are shaken at a constant temperature for several days, and at the end of the incubation period the contents of the flasks are recovered by precipitation with a suitable alcohol such as isopropanol.

For large scale work, it is preferable to conduct the fermentation in suitable tanks provided with an agitator and a means of aerating the fermentation medium. According to this method, the nutrient medium is made up in the tank and sterilized by heating at temperatures of up to about 121° C. Upon cooling, the sterilized medium is inoculated with a previously grown seed of the producing culture, and the fermentation is permitted to proceed for a period of time as, for example, from 2 to 4 days while agitating and/or aerating the nutrient medium and maintaining the temperature at about 30° C. This method of producing S-184 is particularly suited for the preparation of large quantities.

Heteropolysaccharide S-184

The heteropolysaccharide produced by ATCC 53160 is composed principally of carbohydrate, from 12% to 16% protein and from 3.0% to 4.5% (calculated as acetic acid) acyl groups, the carbohydrate portion containing from about 7% to 16% uronic acid and the neutral sugars mannose, glucose and galactose in the approximate molar ratios of 1:3:5.

A summary of the compositional analysis of heteropolysaccharide S-184 is provided in Table 1, below.

TABLE 1

| Analyses | Composition Analysis of Heteropolysaccharide S-184 Sample | | | | |
| --- | --- | --- | --- | --- | --- |
| | BD-1842 | BD-1827 | BD-707 | BD-2117 | BD-2118 |
| % protein (N × 6.25%) | 15.8 | 12.3 | 12.6 | 11.8 | 12.4 |
| % uronic acid (mol. wt. 176, decarboxylation) | 15.8 | 12.3 | 10.76 | 9.0 | 7.1 |
| % acyl | (1) | (1) | (2) | (2) | (2) |
| (as acetic acid) | 3.9 | 3.1 | 4.5 | 3.4 | 3.6 |
| % pyruvate | <0.1 | <0.1 | 0 | 0 | 0 |
| Neutral sugars: | | | | | |
| (% molar ratios) | (3) | (3) | | (4) | (5) |
| mannose | 12 | 12 | | 19.4 (17.9–23.8) | 9.4 (9.3–9.8) |
| glucose | 35.6 | 35 | | 30.1 (27.6–31.9) | 29.2 (28.7–29.5) |
| galactose | 52.4 | 52.5 | | 50.5 (48.5–52.1) | 61.4 (61.1–62.0) |

Notes (1) to (5) represent the analytical procedures described infra.

(1) The acetyl contents were determined by treating a 0.2% aqueous solution of S-184 gum with an alkaline, hydroxylamine reagent followed by treatment with an acidic ferric chloride reagent and colorimetric analysis [See S. Hestrin (1949). *J. Biol. Chem.* 180, 249-261]. Acetyl choline chloride was used as the standard.

(2) The acyl content of from 3.1% to 4.5% (calculated as acetic acid) was determined by an enzymatic assay after hydrolysis of O-acetyl linkages using dilute alkali.

(3) The neutral sugars of S-184 were determined by various techniques. The first method involves hydrolyzing 50 mg of S-184 in 1M $H_2SO_4$ at 100° C. for 4 hours. After cooling, 0.5 ml of 3 mg/ml xylose was added as an internal standard. Samples were neutralized by adding 3 ml of saturated $Ba(OH)_2$, then two drops of Congo Red and $Ba(OH)_2$ until the color changed to red. After centrifuging (20 minutes at 3000 RPM) the supernatants of all samples were evaporated. Dry samples were dissolved in 0.1 ml of hydroxylamine hydrochloride (40 mg/ml) in dry pyridine and heated at 90° C. for 45 minutes. After cooling, 0.1 ml acetic anhydride is added and the sample again heated at 90° C. for 45 minutes. The sugars were separated by gas-liquid chromatography of their aldononitrile acetate derivatives and were identified and quantified by comparison with authentic standards [J. K. Baird, M. J. Holroyde, and D. C. Ellwood (1973) *Carbohydr. Res.* 27, 464-467].

(4) Samples were pretreated by dissolution in 72% $H_2SO_4$ and held for 1 hour at 0° C. prior to dilution and hydrolysis by the first method of neutral sugar analysis described above; results are mean values and ranges obtained for BD-707, BD-2117 and BD-2118.

(5) The neutral sugars of these samples were also characterized by a second method which involves dissolving approximately 2 mg of S-184 in 0.5M trifluoroacetic acid (2 ml). The sample was kept at 100° C. overnight, concentrated to dryness and dissolve in water (2 ml). Sodium borohydride (25 mg) was added and after 2 hours the solution was treated with Dowex 50 ($H^+$) after which the pH dropped to 3.5. After filtration, the solution was concentrated and codistilled with methanol (3 × 5 ml). The residue was dissolved in a mixture of acetic anhydride (1 ml) and pyridine (1 ml), kept at 100° C. for 1 hour and concentrated. After codistillation with toluene (3×5 ml), the residue was dissolved in methylene chloride and analyzed by gas-liquid chromatography. Results are mean values and ranges obtained for BD-707, BD-2117 and BD-2118.

The % uronic acid of the polysaccharide was determined by decarboxylation with 17% hydrochloric acid, followed by trapping the liberated carbon dioxide in standard sodium hydroxide and back tritration [B. L. Browning (1967) *Methods of Wood Chemistry* 2, 632-633].

The absence of pyruvate was determined by adding 1 ml of a 2 mg/ml solution of S-184 to a culture tube, and adding 1 ml of 0.2N HCl, and heating at 100° C. for 4 hours. A 0.5 ml sample of hydrolysate was added to 0.1 ml of reduced nicotinamide adenine dinucleotide (NADH) and 2.4 ml of triethanolamine solution. The absorbance change was measured on a spectrophotometer and pyruvate measured. [Duckworth and Yaphe *Chem. & Ind.* (1970) p. 747.]No significant pyruvate was detected.

Nitrogen analysis was performed by Kjeldahl digestion and was determined to be between approximately 1.9% and 2.5% by weight corresponding to 11.8%-15.8% protein equivalents.

Methylation analysis was performed on partially purified samples of S-184 after dialysis and freeze drying. The samples were methylated according to the procedures outlined in Sandford & Conrad. (1966) *Biochem.* 5, 1508-1507. The O-methyl ether derivatives of the sugars as their aditol acetates were separated by gas chromatography and identified by computer matching with authentic standards. The major methylated sugars identified are shown in Table 2, below.

TABLE 2

Methylated Sugar Residues of S-184

| Identified Sugar Residue | Linkage |
| --- | --- |
| 2, 3, 6 Me₃ Hexitol (Galactose) | 1-4 |
| 2, 3, 6 Me₃ Hexitol (Mannose) | 1-4 |
| 2, 3, 6 Me₃ Hexitol (Glucose) | 1-4 |

It is to be understood that, although the methods of analysis of the heteropolysaccharide described herein were the actual methods used in arriving at the composition described above, other methods of analysis are available to one skilled in the art. Utilization of other methods of analysis should result in the same characterization of the heteropolysaccharide, however, slightly different quantitative results may be reported.

Heteropolysaccharide S-184 has been found to have outstanding properties in aqueous solution, especially in having high viscosity at very low concentrations, good surface activity, good protein compatibility and excellent stabilization/emulsification properties. Because of this, it is useful as a thickening, suspending emulsifying, stabilizing, lubricating film-forming, or binding agent and as a replacement for gum arabic in many applications. S-184 has utility in various industrial and food applications where surface activity and protein compatibility are desirable. In particular it has uses in the following applications or products: adhesives, wall joint cements, water-retentive grouts and mortars, spackling compounds, can sealants, boiler compounds, latex creaming, welding-rod fluxes, braising pastes, ceramic glazes and extrusions, cleaners and polishers, toys, emulsions (latex, asphalt, silicone), silver recovery, seed coatings, spray control for pesticides or herbicides, emulsifiable concentrates and flowable pesticides and herbicides, tobacco binders, water based inks, lithographic fountain solutions, leather finishes, hydromulching and hydro-seeding, textile printing and finishing, wet-end paper additives, wet-end paper retention and formation aids, anti-slick compounds, mold-release agents, liquid resins, slurry and packaged explosives, petroleum and water-well drilling muds, petroleum workover and completion fluids, petroleum stimulation fluids, cosmetics, pharmaceutical suspensions and emulsions.

This gum also has utility in food systems such as jellies and other high sugar systems, beverages including citric acid based drinks, dairy products including ice cream and yogurt, salad dressings, dry mixes, icings, and glazes, syrups, puddings farinaceous foods, canned and retorted foods and bakery fillings.

A particular valuable utility is in the area of food applications especially salad dressing, beverage and dairy products. Heteropolysaccharide S-184 has been found to be particularly useful in foods because of its surface activity, protein compatibility and stabilization/emulsification properties.

A salad dressing was prepared by slurrying heteropolysaccharide S-184 in two to five times its weight of oil, adding the S-184/oil slurry to water and hydrating under vigorous agitation, blending all other dry ingredients and adding them to the water/slurry blend, adding tomato paste and mixing for 3 minutes, adding oleoresin paprika and mixing for 3 minutes adding oil slowly and mixing for 3 minutes, adding vinegar and mixing for 3 minutes, homogenizing using a Colloid Mill and bottling.

S-184 was added as an emulsion stabilizer to the dressing at amounts between about 0.10% and 0.40% by weight. Viscosity, pH, storage stability and texture of the dressing were determined and are shown in Table 3, below.

TABLE 3

Heteropolysaccharide S-184 In Salad Dressing

| Use Level % | Viscosity* mPs (24 hours) | pH | Stability (days) 49° C. (120° F.) | Stability (days) Room Temp | Texture. Flow Property |
| --- | --- | --- | --- | --- | --- |
| 0.10 | 1000 | 3.6 | 7 | 83 | Smooth thin flow |
| 0.15 | 1450 | 3.6 | 31 | 61 | |
| 0.20 | 1650 | 3.6 | 26 | 71 | Smooth, creamy |
| 0.25 | 2700 | 3.6 | 33 | Over 365 | Stable, acceptable |
| 0.40 | 4700 | 3.6 | Not tested | | Semi-gelled, unacceptable |

Heteropolysaccharide S-184 has a particular profile of solution properties that is a distinctive characteristic of this polysaccharaide and which enables it to be distinguished over other heteropolysaccharides. S-184 has the following profile of properties:

1. VISCOSITY AND SHEAR

| | Syn. Tap H₂O* | Syn. Tap H₂O* + 0.1% KCl |
|---|---|---|
| A. Brookfield | | |
| 1. 1.0% | | |
| @ 60 rpm | 1080 cps | 1030 cps |
| @ 6 rpm | 6000 cps | |
| Spindle No. | 3 | |
| 2. 0.1% (UL adapter @ 6 rpm) | 7 cps | 7 cps |
| 3. 0.5% Wells-Brookfield @ 9.6 sec$^{-1}$ | 330 cps | 320 cps |
| 4. 1.0% DI H₂O @ 60 rpm | 1460 cps | |
| Spindle No. | 3 | |
| B. Shear (Wells-Brookfield) | | |
| 1. η @ 1.92 sec$^{-1}$ 4100 cps | | |
| 2. η @ 9.6 sec$^{-1}$ 1270 cps | | |
| 3. η @ 76.8 sec$^{-1}$ 290 cps | | |
| 4. η @ 384 sec$^{-1}$ greater than 60 cps (Initial) | | |
| 5. η @ 384 sec$^{-1}$ greater than 60 cps (5 min.) | | |
| 6. η @ 9.6 sec$^{-1}$ 1180 cps | | |
| C. 40° F. Storage (Brookfield) | | |
| 1320 cP @ 60 rpm with spindle No. 3; no gelation. | | |

2. SALT AND DYE COMPATABILITY

| A. Salt | |
|---|---|
| 1. CaCl₂ (Saturated) | Compatible |
| 2. Amm. polyphosphate | Precipitate |
| 3. 60% NH₄NO₃ | Compatible |
| 4. 1% Al₂(SO₄)₃.18H₂O | Compatible |
| 5. 1% CaCl₂.2H₂O | Compatible |
| 6. 1% KCl | Compatible |
| B. Dyes | |
| 1. Milling Green | Compatible |
| 2. Methylene Blue | Compatible |

*Deionized water containing 1000 ppm NaCl and 147 ppm CaCl₂.2H₂O.

Description of the Strain

Heteropolysaccharide S-184 may be prepared by fermentation of a suitable nutrient medium with an unnamed Alcaligenes species. A deposit under the Budapest Treaty of a biologically pure culture of the microorganism employed in making this heteropolysaccharide was made with the American Type Culture Collection, Rockville, Md., on Jun. 19, 1985 under Accession No. ATCC 53160.

A. Characteristics of Colony Morphology

On nutrient agar isolate S-184 forms round colonies with opaque centers and translucent edges. The pigmentation is white to grey. Colonies are 1-3 mm after 72 hours at 30° C.

B. Characteristics of Cell Morphology

The cells are gram-negative, long rods (0.8-2.3 μm) with vacuoles present. The flagella arrangement was mixed as polar, lateral and peritrichous forms were observed. The organism was observed to produce a pinkish pigment under some growth conditions.

C. Physiological and Biochemical Characteristics

The physiological and biochemical test results are given in Table 4, below. The organism is cytochrome oxidase positive, catalase positive and oxidative in metabolism. The results were positive for citrate utilization and production of H₂S. It has the ability to hydrolyze starch, gelatin, casein and polysorbate 80, USP (a surface active agent available from Difco). It will grow well at 30° C. and 37° C. but was not tested at higher temperatures. It can tolerate 1.5% NaCl but not 3% and will grow in the pH range of 6-10.

Its pattern of acid production from carbohydrates is shown below:

| Acid Production |
|---|
| L-Arabinose |
| Fructose |
| Galactose |
| Maltose (weak) |
| Mannitol (weak) |
| Mannose |
| No acid production |
| Adonitol |
| Dulcitol |
| Ethanol |
| D-Glucose |
| D-Xylose |
| Inositol |
| Inulin |
| Lactose |
| Melibiose |
| α-Methylglucoside |
| Raffinose |
| Rhamnose |
| Salicin |
| Sorbitol |
| Sucrose |
| Trehalose |
| D-Xylose |

S-184 was able to utilize the following 46 substrates as sole carbon and energy sources:

D-Xylose
L-Arabinose
D-Glucose
D-Mannose
D-Galactose
D-Fructose
Maltose
Cellobiose
Inulin
Gluconate
Saccharate
Mucate
Acetate
Propionate
Butyrate
Caproate
Heptanoate
Caprylate
Pelargonate
Caprate
Malonate
Succinate
Fumarate
L-Malate
DL-β-Hydroxybutyrate
DL-Lactate
DL-Glycerate
Citrate
α-Ketoglutarate
Pyruvate
Laevulinate
Mannitol
Glycerol
D-α-Alanine
β-Alanine
L-Threonine
L-Leucine
DL-Isoleucine
L-Aspartate
L-Glutamate
L-Lysine
DL-Ornithine
L-Histine
L-Proline -continued L-Tyrosine
L-Phenylalanine

TABLE 4

Physiological and Biochemical Test Results of Strain S-184

| | |
|---|---|
| Cytochrome oxidase | + |
| Catalase | + |
| OF tests | Oxidative |
| Anaerobic growth | − |
| TSI agar: Slant | NC |
| Indole | − |
| Methyl Red | − |
| Voges-Proskauer | − |
| Simmons' citrate | + |
| Nitrite reduction | − |
| Nitrate reduction | − |
| Litmus milk | NC |
| Arginine dehydrolase | − |
| Lysine decarboxylase | − |
| Ornithine decarboxylase | − |
| Phenylalanine deaminase | NG |
| Ammonia from Peptone | − |
| Urease | − |
| H$_2$S (from peptone, cystine and sulfite medium) | + |
| 3-Ketolactose | − |
| Congo Red absorption | − |
| Phosphatase | − |
| Haemolysis (sheep blood) | NT |
| Egg yolk reaction | ± |
| Starch hydrolysis | + |
| Gelatin hydrolysis | + |
| Casein hydrolysis | + |
| Esculin hydrolysis | − |
| Polysorbate 80 hydrolysis | + |
| Growth at various temperatures: | |
| 4° C. | − |
| 30° C. | + |
| 37° C. | + |
| Growth at various NaCl concentrations: | |
| 1.5% (W/V) | + |
| 3.0% (W/V) | − |
| 6.5% (W/V) | − |
| 7.5% (W/V) | − |
| 10.0% (W/V) | − |
| Growth at various pH values: | |
| 4 | − |
| 6 | + |
| 8 | + |
| 10 | + |
| 11 | + |
| 12 | − |

NG = No Growth
NC = No change
NT = Not tested
+ = positive
− = negative

Since the organism was strictly aerobic, gram negative, and showed mixed flagellation, it was classified as belonging to the genus Alcaligenes, according to the 8th edition of Bergey's Manual of Determinative Bacteriology (1974).

The genus Alcaligenes was redefined in the latest Bergey's Manual (Bergey's Manual of Systematic Microbiology, Vol. 1, 1st Edition, 1984) to exclude all pigmented organisms. Isolate S-184 fits within this newly defined genus but does not belong to either of the two species listed which are *Alcaligenes faecalis*, *Alcaliogenes denitrificans* subspecies denitrificans and *Alcaligenes denitrificans* subspecies xylosoxidans. S-184 is thus a new species of Alcaligenes.

Other embodiments of the present invention will be apparent to one skilled in the art from a consideration of this specification. It is intended, therefore, that the specification and examples be considered as exemplary only, with the true scope and spirit of the invention being indicated by the following claims.

EXAMPLE 1

A YM flask seed was started from a 48-hour nutrient agar culture placed on a gyrotary shaker at 30° C. Approximately 24 hours later, this seed was used to inoculate a flask containing E$_1$ medium with 3% hydrolyzed starch as the carbon source. This flask was also placed on a gyrotary shaker at 30° C. Approximately 72 hours later, this flask was noted to have viscous beer, and upon addition of 2 volumes of 99% isopropyl alcohol, a fibrous precipitate was noted.

E$_1$ medium contains 5 g of dipotassium phosphate, 0.1 g of magnesium sulfate, 0.9 g of ammonium nitrate, 0.5 g of promosoy 100 (an enzymatic digest of soybean meal sold by Central Soya Chemurgy Division), 30 g of dextrose and 1 L of tap water. The pH of the E$_1$ medium is about 7.6–7.8.

Another YM seed flask was prepared in the above fashion and used at 24 hours to inoculate 4 flasks containing various media and these flasks were incubated at 30° C. on a gyrotary shaker for about 72 hours at which time the pH, viscosity, gum yield and product viscosity were measured. The results are shown in Table 5 below.

TABLE 5

Effect of Media on Gum Production

| Medium | Carbon Source | pH | Beer Vis (cP) | % Gum Yield | DI Water Prod Vis (cP) 1%/0.1% | 1% KCL Prod Vis (cP) 1%/0.1% |
|---|---|---|---|---|---|---|
| E$_1$ | 3% glucose | 6.8 | 7600 | 1.702 | 1900/15 | 1100/7 |
| E$_1$ (-NH$_4$NO$_3$ + 0.19% NaNO$_3$) | 3% glucose | 7.6 | 7400 | 1.840 | ND | ND |
| E$_1$ (containing 0.2% Promosoy) | 3% glucose | 6.9 | 7200 | 1.762 | ND | ND |
| E$_1$ + Hole Salts[2] | 3% glucose | 6.9 | 2900 | 1.266 | ND | ND |

[1]ND: Not determined
[2]Hole salts are prepared by adding the following ingredients to one liter of deionized or distilled water:
H$_3$BO$_3$      285 mg
MnCl$_2$.4H$_2$O      1800 mg
FeSO$_4$      1360 mg TABLE 5-continued Effect of Media on Gum Production

| Medium | Carbon Source | pH | Beer Vis (cP) | % Gum Yield | DI Water Prod Vis (cP) 1%/0.1% | 1% KCL Prod Vis (cP) 1%/0.1% |
|---|---|---|---|---|---|---|
| $CuCl_2$ | 26.9 mg | | | | | |
| $ZnCl_2$ | 20.8 mg | | | | | |
| $CoCl_2$ | 40.4 mg | | | | | |
| $Mg_2MoO_4.2H_2O$ | 25.2 mg | | | | | |
| Sodium tartrate | 1770 mg | | | | | |

This stock solution is added to media at 1 ml/L.

As seen from the above results, the best growth medium is $E_1$ with 3% glucose.

EXAMPLE 2

A fermentation procedure for producing large quantities of heteropolysaccharide S-184 is provided.

A 500 ml Erlenmeyer flask containing 100 ml of YM broth (Difco) was inoculated with a loopful of S-184 cells from a 48-hour nutrient agar plate. The flask was incubated for 24 hours at 30° C. on a gyrotary shaker set at 400 rpm. A 1% inoculum was then made into two 500 ml Erlenmeyer flasks containing 100 ml each of seed medium. The seek medium contained:

| Glucose | 3% |
|---|---|
| $K_2HPO_4$ | 0.5% |
| $NH_4NO_3$ | 0.09% |
| $MgSO_4.7H_2O$ | 0.01% |
| Promosoy 100 | 0.05% |

The medium was prepared in tap water. These flasks were incubated at 30° C. on a gyrotary shaker at 400 rpm for 24 hours at which point they were used to inoculate a 5 L fermentor vessel containing 3000 ml (final volume) of the same medium. The fermentation was controlled at 30° C. and the aeration rate at 1 L/minute. The agitation was started at 400 rpm and increased thereafter to ensure good mixing. At 24 hours approximately 2.5 L of this seed were used to inoculate a 30 L fermentor containing 20 L (final volume) of the following medium:

| Glucose | 3.0% |
|---|---|
| $K_2HPO_4$ | 0.05% |
| $NH_4NO_3$ | 0.09% |
| $MgSO_4.7H_2O$ | 0.01% |
| Promosoy 100 | 0.05% |
| $Fe^{++}$ | 1 ppm |
| Sag 5691 (a defoaming agent supplied by Union Carbide) | 0.005% |

The temperature was maintained at 30° C. and the aeration rate at 5 L/minute until 22 hours into the fermentation where it was adjusted to 10 L/minute. It remained at that rate for the remainder of the fermentation. The pH was controlled at greater than 6.3 by the addition of 40% KOH as needed using an automatic pH control system. The agitation was initially set at 300 rpm and was increased to 400 rpm at 22 hours and to 700 rpm at 45 hours. It remained at 700 rpm for the remainder of the fermentation. The results of this fermentation are given in Table 6 below.

TABLE 6

| Age | pH | Beer Viscosity | Gum Yield (g/100 ml) | Residual Carbon Source (%) |
|---|---|---|---|---|
| 0 hours | 7.0 | ND | ND | 3.0 |
| 22 hours | 6.3 | 620 cP | ND | ND |
| 45 hours | 6.9 | 4200 cP | 1.26 | 0.41 |
| 68 hours | 7.2 | 5100 cP | 1.37 | less than 0.1 |

ND = No data

The fermentation liquor was heated to approximately 75° C. for 15 minutes and then cooled to approximately 30° C. The fermentation liquor was added to three volumes of 99% isopropanol. The polysaccharide precipitated as a fibrous material which was easily recovered using a sieve. The fibers were dried in a forced air tray drier at 140° F. for 2.5 hours before being milled to a powder.

EXAMPLE 3

A 500 ml Erlenmeyer flask containing 100 ml of YM broth (Difco) was inoculated with a loopful of S-184 cells from a 48-hour nutrient agar plate. The flask was incubated for 24 hours at 30° C. on a gyrotary shaker set at 400 rpm. A 1% inoculum was then made into five 500 ml Erlenmeyer flasks containing 100 ml each of seed medium. The seed medium contained:

| Glucose | 3% |
|---|---|
| $K_2HPO_4$ | 0.5% |
| $NH_4NO_3$ | 0.09% |
| $MgSO_4.7H_2O$ | 0.01% |
| Promosoy 100 | 0.05% |
| $Fe^{++}$ | 1 ppm |
| Tap Water | |

These flasks were incubated at 30° C. on a gyrotary shaker at 400 rpm for 24 hours at which point they were used to inoculate a 14 L fermentor vessel containing 10 L (final volume) of the final medium. The fermentation was controlled at 30° C. and the aeration rate at 3 L/minute. The agitation was started at 400 rpm and increased thereafter to ensure good mixing. The final medium consisted of:

| Glucose | 3.0% |
|---|---|
| $K_2HPO_4$ | 0.05% |
| $NH_4NO_3$ | 0.09% |
| $MgSO_4.7H_2O$ | 0.01% |
| Promosoy 100 | 0.05% |
| $Fe^{++}$ | 1 ppm |

The pH was controlled at >6.5 by the addition of 25% KOH as needed using an automatic pH control system. The results of this fermentation are given in Table 7 below:

TABLE 7

| Age (hrs.) | pH | Beer Viscosity | Gum Yield (gm/100 ml) | Residual Carbon Source |
|---|---|---|---|---|
| 0 | 7.3 | ND | ND | 3.15% |
| 21 | 7.05 | 20 cp | 0.65% | 1.59% |
| 45 | 6.9 | 3450 cP | 1.22% | 0.48% |
| 78 | 7.1 | 2550 cp | 1.50% | less than 0.10% |

ND = No data

The fermentation liquor was heated to approximately 75° C. for 15 minutes and then cooled to approximately 30° C. The fermentation liquor was added to three volumes of 99% isopropanol, the polysaccharide precipitated as a fibrous material which was easily recovered using a sieve. The fibers were dried in a forced air tray drier at 140° F. for 2.5 hours before being milled to a powder.

What is claimed is:

1. Heteropolysaccharide S-184, consisting essentially of carbohydrate, substantially no pyruvate, from 12% to 16% protein and from 3.0% to 4.5% acyl groups calculated as acetic acid, the carbohydrate portion containing from about 7% to 16% uronic acid, and the neutral sugars mannose, glucose, and galactose in the approximate molar ratios of 1:3:5.

2. The heteropolysaccharide S-184 of claim 1, produced by a biologically pure culture of Alcaligenes ATCC No. 53160 in an aqueous nutrient medium by aerobic fermentation of an assimilable carbon source at a pH greater than 6.3 and a temperature of 30°–75° C.

* * * * *